US012059168B2

United States Patent
Orozco Castillo

(10) Patent No.: US 12,059,168 B2
(45) Date of Patent: Aug. 13, 2024

(54) SYSTEMS AND METHODS FOR BALL PROBE ULTRASONIC FORAMINOTOMY

(71) Applicant: Ludwig David Orozco Castillo, Parker, TX (US)

(72) Inventor: Ludwig David Orozco Castillo, Parker, TX (US)

( * ) Notice: Subject to any disclaimer, the term of this patent is extended or adjusted under 35 U.S.C. 154(b) by 365 days.

(21) Appl. No.: 17/348,844

(22) Filed: Jun. 16, 2021

(65) Prior Publication Data

US 2022/0401120 A1   Dec. 22, 2022

(51) Int. Cl.
*A61B 17/32* (2006.01)

(52) U.S. Cl.
CPC ........... *A61B 17/320068* (2013.01); *A61B 2017/32007* (2017.08); *A61B 2017/320078* (2017.08); *A61B 2017/32008* (2013.01)

(58) Field of Classification Search
CPC .. A61B 17/320068; A61B 2017/32007; A61B 2017/320073
See application file for complete search history.

(56) References Cited

U.S. PATENT DOCUMENTS

| 4,019,254 | A | * | 4/1977 | Malmin | A61C 5/42 433/102 |
| 4,981,143 | A | * | 1/1991 | Sakita | A61B 10/0291 600/570 |
| 5,915,964 | A | * | 6/1999 | Walia | A61C 5/42 433/102 |
| 5,964,761 | A | | 10/1999 | Kambin | |
| 5,976,105 | A | | 11/1999 | Marcove et al. | |
| 7,229,455 | B2 | * | 6/2007 | Sakurai | A61B 17/320092 606/128 |

(Continued)

FOREIGN PATENT DOCUMENTS

| CN | 204219006 | 3/2015 |
| CN | 204233246 | 4/2015 |

(Continued)

OTHER PUBLICATIONS

Khoo, Palmer, Laich, Fessler, "Minimally Invasive Percutaneous Posterior Lumbar Interbody Fusion," Neurosurgery—Online, Nov. 2002, vol. 51, Supplement 2, Chapter 21.

(Continued)

*Primary Examiner* — Nicholas W Woodall
(74) *Attorney, Agent, or Firm* — Regitz Mauck PLLC; Dustin Mauck; Mike Regitz

(57) ABSTRACT

The present invention discloses a ball probe ultrasonic bone removal device that is designed to assist surgeons with foraminotomy procedures. The device comprises a shaft at a first end of the device and a spherical ball tip at a second end of the device. In between the shaft and the ball tip is a foot piece that connects to the shaft through an angle. On the foot piece, serrations or a coarse surface cover a portion of the circumference of the foot piece. In some embodiments, serrations or a coarse surface may also cover a portion of the circumference of the shaft. The spherical ball tip is smooth and designed to cause no damage to the sensitive nerves and tissue in the intervertebral foramina, but the surface with the serrations or the coarse protrusions are designed to remove bone and tissue under ultrasonic movement (e.g., vertical vibration, rotational oscillation).

18 Claims, 14 Drawing Sheets

(56) References Cited

U.S. PATENT DOCUMENTS

| | | | |
|---|---|---|---|
| 8,236,019 B2* | 8/2012 | Houser | A61B 17/320068 |
| | | | 606/169 |
| 8,353,912 B2 | 1/2013 | Darian et al. | |
| 8,613,746 B2 | 12/2013 | Spratt et al. | |
| 8,709,087 B2 | 4/2014 | Cragg | |
| 9,232,953 B2 | 1/2016 | Bono et al. | |
| 9,289,227 B2 | 3/2016 | Lauchner | |
| 9,408,624 B2 | 8/2016 | Molinari et al. | |
| 9,408,716 B1 | 8/2016 | Reitblat et al. | |
| 9,504,483 B2 | 11/2016 | Houser et al. | |
| 9,510,875 B2 | 12/2016 | Reitblat et al. | |
| RE46,432 E | 6/2017 | Kingsley et al. | |
| 10,016,208 B2* | 7/2018 | Gouery | A61B 17/320068 |
| 10,105,232 B2 | 10/2018 | Roche et al. | |
| 2004/0023187 A1* | 2/2004 | Hickok | A61C 3/03 |
| | | | 433/119 |
| 2004/0039384 A1 | 2/2004 | Boehm et al. | |
| 2004/0199192 A1* | 10/2004 | Akahoshi | A61F 9/00745 |
| | | | 606/169 |
| 2006/0206118 A1 | 9/2006 | Kim et al. | |
| 2010/0256682 A1 | 10/2010 | Fallin et al. | |
| 2010/0286486 A1 | 11/2010 | Parker et al. | |
| 2011/0250560 A1* | 10/2011 | Kwon | C04B 35/638 |
| | | | 433/119 |
| 2013/0253591 A1 | 9/2013 | Kornel | |
| 2014/0277145 A1 | 9/2014 | Reitblat et al. | |
| 2014/0277499 A1 | 9/2014 | Ainsworth et al. | |
| 2015/0230834 A1 | 8/2015 | Cannestra | |
| 2015/0374354 A1 | 12/2015 | Boyd et al. | |
| 2016/0157885 A1 | 6/2016 | Lauchner | |
| 2017/0209158 A1 | 7/2017 | Williams | |
| 2019/0247069 A1* | 8/2019 | Fujisaki | A61B 17/16 |
| 2019/0247070 A1* | 8/2019 | Araki | A61B 17/32 |
| 2020/0129188 A1* | 4/2020 | Scifert | A61B 17/320068 |

FOREIGN PATENT DOCUMENTS

| | | |
|---|---|---|
| CN | 104905850 | 4/2017 |
| KR | 20060094733 | 8/2006 |
| WO | WO2007120903 | 10/2007 |

OTHER PUBLICATIONS

Xiao, Xiong, Zhang, Jian, Zheng, Luo, Dai, Zhang, "Percutaneous Posterior-Lateral Lumber Interbody Fusion for Degenerative Disc Disease Using a B-Twin Expandable Spinal Spacer," Springer, Sep. 26, 2009.

* cited by examiner

SYSTEMS AND METHODS FOR BALL PROBE ULTRASONIC FORAMINOTOMY

TECHNICAL FIELD

The present invention relates generally to systems and apparatuses that assist with foraminotomy or the removal of portions of the intervertebral foramina in order to alleviate foraminal stenosis, and more specifically, to the systems and methods for using a single ball probe instrument with the capability of ultrasonic bone or tissue removal for a foraminotomy procedure.

BACKGROUND OF THE INVENTION

Back and spinal problems affect countless patients in the United States and throughout the World and foraminal stenosis is a condition related to the narrowing of the nerve root foraminae caused by enlargement of the joint material, ligamentum flavum, or bone spurs. Due to this enlargement, the nerve roots that exit the spinal column through the neural foramina may become compressed due the reduced space in the intervertebral foramina. Many times this condition is due to a ankylosed (auto-fused), degenerated vertebrae within the lumbar, thoracic, or cervical regions of the spine. This type of nerve compression can lead to pain, numbness, weakness, and in certain cases paralysis. Due to these issues, a foraminotomy may be performed to clear out the space in the intervertebral foramina and improve the quality of life for a patient. However, any surgery affecting or surrounding the spine becomes very serious due to risks of damaging the spinal cord and the nerves that connect to the spinal cord. One wrong move or improper cut may lead to grave consequences for the rest of the patient's life.

Thus, doctors and medical device companies continue to advance the treatment and surgical procedures offered for foraminal stenosis. The spine and corresponding vertebrae were designed to protect the spinal cord and connected nerves, so it can be difficult to access the desired area for this procedure. Different procedures that involve different tools, systems, devices, and methods have been developed and there are numerous considerations to weigh when choosing a procedure. For example, does the surgeon want to access the desired vertebrae from the anterior or posterior of the patient? How large should the incisions be for the surgery? Since the intervertebral foramina can be difficult to view or access, how will the surgeon view the surgical area? How can the length of surgery be decreased? How can the recovery time for the patient be improved? With these considerations in mind, a number of different procedures have been developed. And different devices and apparatuses accompany each different method.

Current options to re-open or expand the space in the foramen suffer from various drawbacks due to the small space, the awkward angle involved, and the importance of the bones, tissues, and nerves surrounding the foramina. With respect to devices that can remove or displace the bone, cartilage, ligament, and tissue within the foramina, Kerrison rongeurs are commonly used. However, this tool can be time-consuming to use and difficult to properly place into the foramen space and displace the desired tissue and bone. Other devices like a gigli saw were used for this procedure but proved to be unsafe with paraspinal soft tissues. The gigli saw is now off the market. Another device that is used for this procedure resembles a drill with an angle, where the drill bit is housed in a protective sheath. In practice, this device proves to be bulky due to the additional diameter required for the sheath and ineffective due to the rotational movement of the drill. A device that does not suffer from these drawbacks is desired.

Other procedures have been developed to address foraminal stenosis, but these are more significant surgical procedures that can lead to further complications and longer recovery times. For example, a facetectomy can be used to treat this condition, but it involves a total removal of the facet joint including the back wall of the foramen. This procedure is time-consuming, involves higher blood loss, and can produce iatrogenic instability. Interbody fusion of multiple vertebrae has also been used to treat foraminal stenosis. This procedure relies on indirect decompression by increasing the vertical size of the foramen but is ineffective if the stenosis is due to an ankylosed (auto-fused) segment or facet. Using an interbody fusion to treat foraminal stenosis is also a significant procedure that is time-consuming and involves higher blood loss.

Due to the manner of accessing the foramina and the circumstances surrounding each procedure, different devices, apparatuses, systems, and methods have been developed to accomplish a foraminotomy. However, each method has its drawbacks and problems, including inefficiencies, health risks, longer recovery times, and other concerns. Patients with back and spinal problems need a new solution that addresses these drawbacks and improves the outcome for the patient.

BRIEF SUMMARY OF THE INVENTION

The present invention includes novel medical devices for use in foraminotomies. Ball probe devices have been used by surgeons in the past to evaluate or determine the available space in the intervertebral foramina. Without sufficient space, the exiting nerve roots of the patient may become compressed. Bone, tissue, cartilage, ligament, and other materials may then need to be removed from the intervertebral foramina to free up the exiting nerve roots and alleviate this compression. Ultrasonic bone removal devices have been used by surgeons in the past to remove bone, tissue, and cartilage, but these devices are not capable of assessing the degree of foraminal stenosis (i.e., patency of the foramen).

The present invention discloses a novel device that combines the ball probe device, which has not been used to remove bone and tissue, and ultrasonic bone removal concepts, which have not been used in combination. In some embodiments, the ball probe ultrasonic bone removal device includes a shaft at a first end of the device and a spherical ball tip at a second end of the device. In between the shaft and the ball tip is a foot piece that connects to the shaft through an angle. In some embo ents, that angle between the foot piece and the shaft is 90-120 degrees. On the foot piece, serrations or a coarse surface (with protrusions) cover a portion of the circumference of the foot piece. The spherical ball tip is smooth and designed to cause no damage to the sensitive nerves and tissue in the intervertebral foramina, but the surface with the serrations or the coarse protrusions are designed to remove bone and tissue under ultrasonic movement (e.g., vertical vibration, rotational oscillation). The serrations and coarse surface of the foot piece can take many different forms.

The coverage of the serrations or the coarse surfaces on the foot piece may differ based upon the procedure. The serration or coarse surfaces may cover one half, one third, or one fourth of the circumference of the foot piece. The serrations or coarse surfaces may also extend from the foot piece, across the angle, and to the shaft. The angle that connects the foot piece to the shaft may also adjust from 90 degrees-120 degrees in some embodiments. The size of the sphere on the ball tip may also come in different sizes. These variations enable the surgeon to accomplish numerous different types of procedures on different patients.

The ball probe ultrasonic bone removal device may also have an interface between the shaft and a handle that enables a surgeon to change from one ball probe/foot piece attachment to another. These attachments may be disposable, while the handle of the ball probe ultrasonic bone removal device may be used multiple times. Suction and irrigation features are also disclosed to enable the removed bone and tissue to be extracted from the intervertebral foramina. The device may also be controlled (e.g., on/off, speed of ultrasonic movement, depth of device, suction, irrigation) through input buttons or screens on the device or through a wired or wireless connection to the device.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
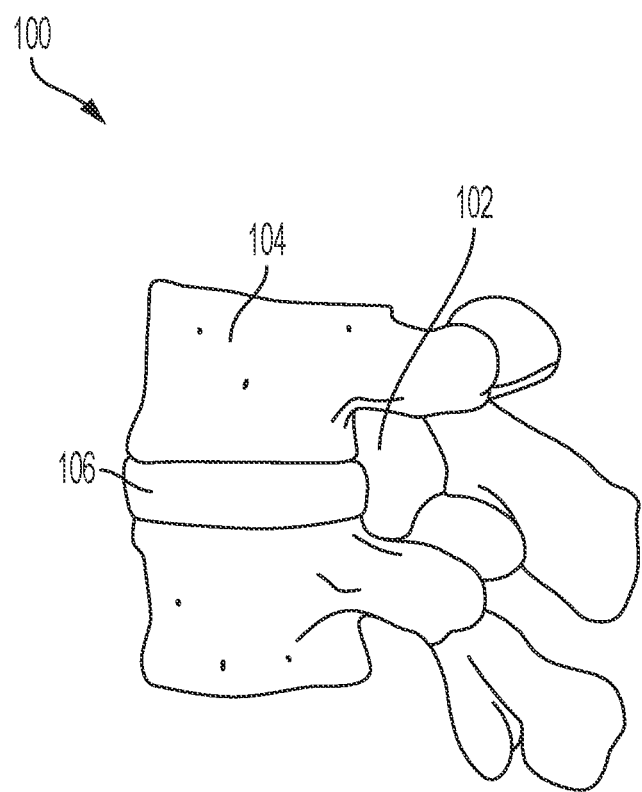
FIG. 1 shows a lateral view of a portion of a spine of a patient.

FIG. 1 shows a lateral view of a portion of the spine of a patient 100 including two vertebrae. A vertebral body 104 and the remaining vertebrae of a human spine protect the nerves of the spinal column (not shown) of a patient. The human spine and the corresponding vertebrae are tasked with the extremely important job of protecting the nerves of the spinal column. An anulus fibrosus 106 is the tough circular exterior of the intervertebral disc that separates neighboring vertebral bodies 104 down the spine of a patient. The anulus fibrosus 106 and the intervertebral discs are designed to protect the spinal column as well, but also designed to provide some movement and flexibility between the vertebral bodies 104 of the spine. As seen in FIG. 1, a posterior portion of the vertebral body 104 is a circular portion of solid bone, while an anterior portion of the vertebral body 104 defines a space or an intervertebral foramina 102. The protected nerves of the spinal column can exit through this intervertebral foramina 102 and travel to other areas of the body, such as the arms or legs. The brain can communicate with the various portions of the human body through the spinal nerves. Thus, it is imperative that the nerves from the spinal column are unimpeded and protected as they exit the spinal column and enter the remaining areas of human body.

Figure 2:
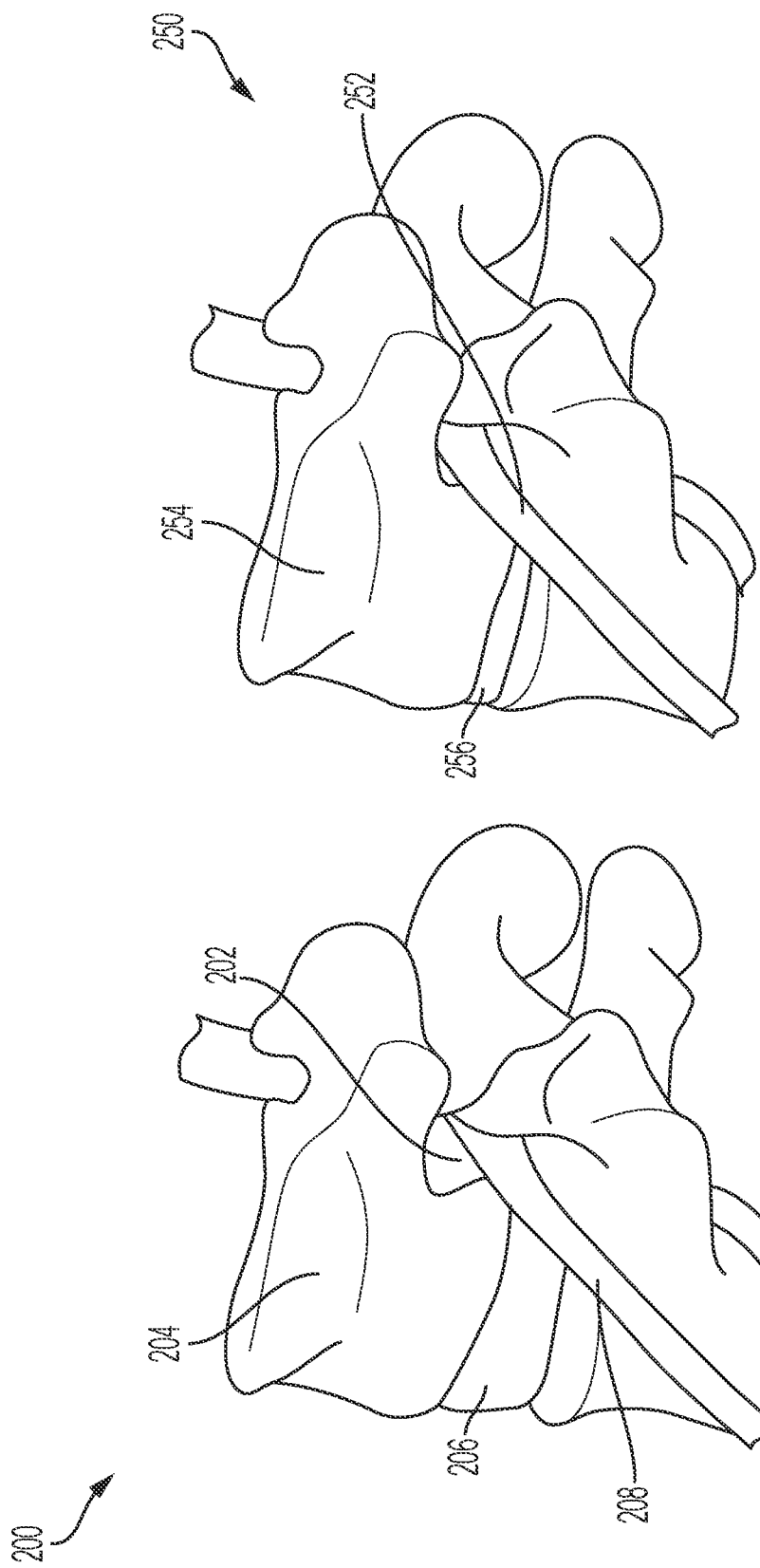
FIG. 2 shows two lateral views of a portion of the spine of a patient with a normal foraminal space and a foraminal space exhibiting foraminal stenosis.

FIG. 2 shows two lateral views of a portion of the spine of a patient with a normal foraminal space 200 and a foraminal space exhibiting foraminal stenosis 250. Once again, vertebral bodies 204, 254 protect the spinal column of a human spine. Anulus fibrosus 206, 256 are the tough circular exterior of the intervertebral discs that separate neighboring vertebral bodies 204, 254. To build on FIG. 1, a nerve root 208 is shown exiting an intervertebral foramina 202 of the neighboring vertebral bodies 204. When the intervertebral foramina 202 is open and unobstructed, the nerve root 208 exits the vertebral body 204 without experiencing compression. However, a nerve root 252 is also shown exiting the intervertebral foramina 202, but there is limited space for the nerve root 252 to exit. This leads to compression of the nerve root 252 by the vertebral bodies 254. Many times, this reduction in space within the intervertebral foramina 202 and compression of the nerve root 252 can be attributed to the degeneration of the intervertebral disc within the annulus fibrosus 256, or the overgrowth of the facet joints, ligamentum flavum, or bone spurs. This type of nerve compression can lead to pain, numbness, weakness, and in certain cases paralysis. For example, if there is compression on a exiting nerve root 252 that leads to a patient's leg, then the patient may feel pain, numbness, weakness, or even paralysis in that leg.

Figure 3:
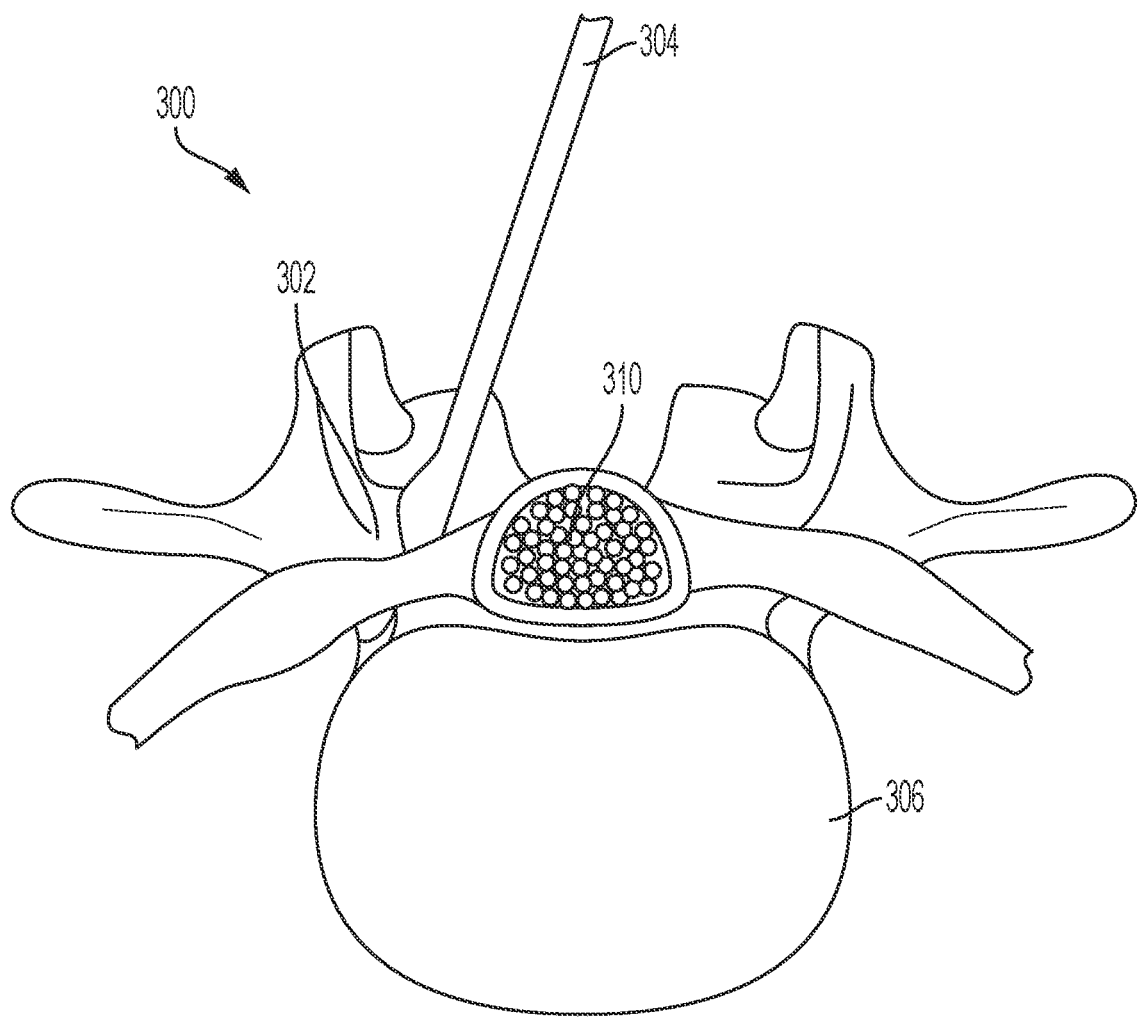
FIG. 3 shows a top view of a portion of the spine of a patient showing a vertebral body, a spinal canal, an intervertebral foramina, and an exiting nerve root.

FIG. 3 shows a top view of a portion of the spine 300 of a patient showing an intervertebral foramina 302, exiting nerve root 304, vertebral body 306, and a spinal canal 310. This view better shows the spinal canal 310 and the nerve rootlets that run through the spinal canal 310. The human spine is designed to protect the nerves of the spinal canal 310. As mentioned above, the vertebral body 306 is a circular shaped bone on the posterior of the patient but is configured to allow the exiting nerve roots 304 of the spinal canal 310 to reach other portions of the patient's body. The intervertebral foramen 302 provides the space and opening for the exiting nerve roots 304 to escape the spinal canal 310. However, due to the importance of the exiting nerve roots 304, the intervertebral foramen 302 provides a limited space for the exiting nerve roots 304. As mentioned above, when degeneration of the intervertebral disc or the overgrowth of the facet joints, ligamentum flavum, or bone spurs leads to a reduced intervertebral foramen 302, the exiting nerve roots 304 may be compressed, which can lead to serious complications to the patient.

Figure 4:
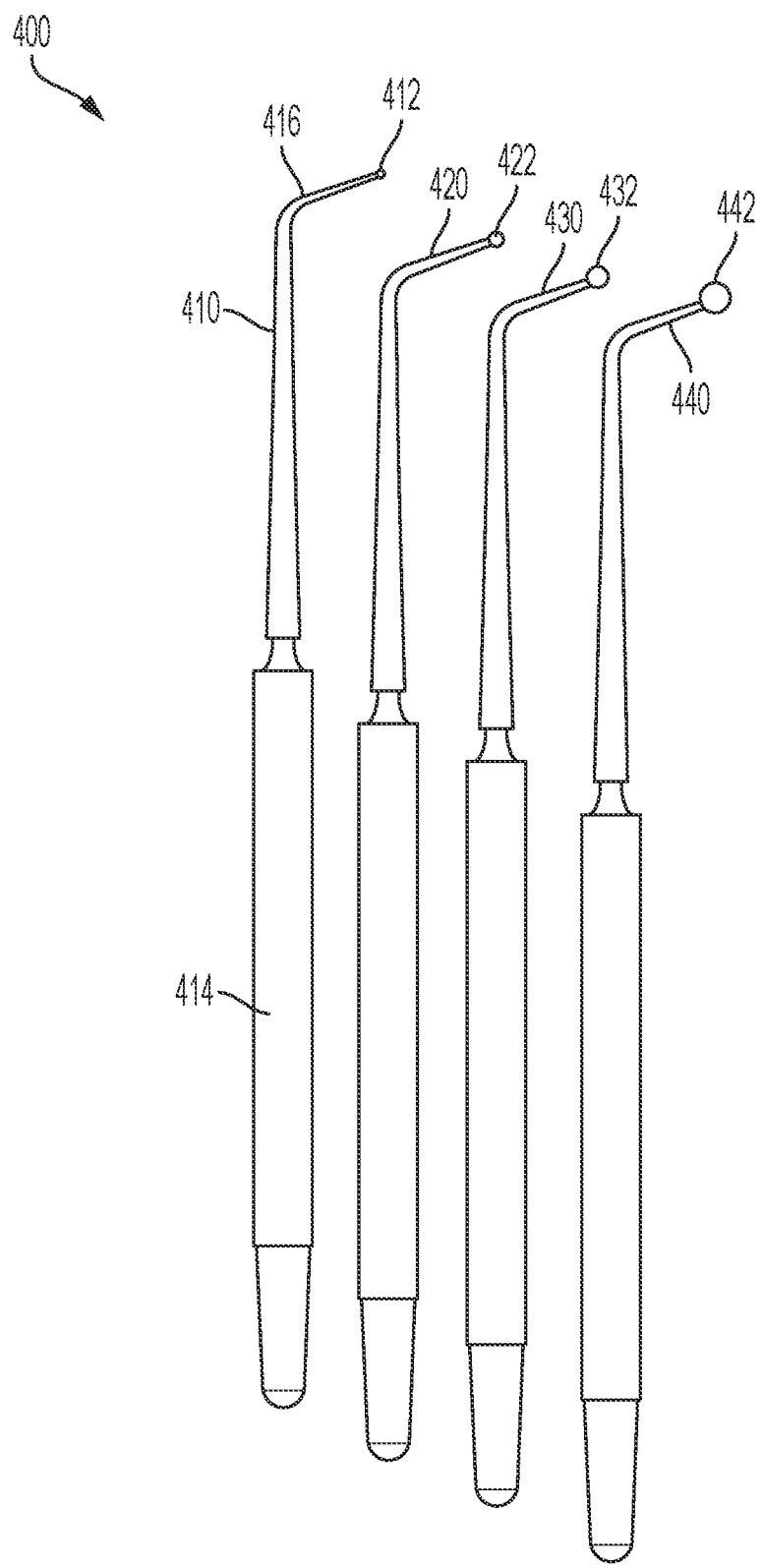
FIG. 4 shows numerous ball probe devices that have been used in prior methods to evaluate a space in the intervertebral foramina.

As shown in FIG. 2, the intervertebral foramen 202 offers a circular opening if a surgeon is accessing it from a side of the vertebral body 204. That circular opening may be open, minimally obstructed, obstructed, or even closed. The amount of space available in the intervertebral foramen 202 determines whether there may be any compression on the exiting nerve roots 208, 252. FIG. 4 shows numerous ball probe devices 400 that have been used in prior methods to evaluate a space in the intervertebral foramina. With access to the intervertebral foramina, a surgeon may use one or more ball probe devices 400 to test the circular space available within the intervertebral foramina. A first ball probe device contains a handle 414, a shaft 410, a foot piece 416, and ball probe 412 (or ball tip portion) at the end of the device. The handle 414 is held by the surgeon when probing the intervertebral foramina. The shaft 410 provides a length from handle 414 to ball probe 412 to allow the surgeon to manipulate the ball probe device 400 to properly access the intervertebral foramina. The foot piece 416 connects to the shaft 410 through an angle that enables the surgeon to manipulate the ball probe device 400 to properly access the intervertebral foramina. This angle of the foot piece 416 can vary so that the surgeon can get the proper angle to access the intervertebral foramina. In use, the ball probe 412 may enter or be blocked from entering the intervertebral foramina and provide the surgeon with an idea of the space available to access the intervertebral foramina. Due to its small size, ball probe 412 may suggest an obstructed opening to the intervertebral foramina.

As shown in FIG. 4, a larger sized ball probe 422 is provided with a different angled connection to the foot piece 420. Then a larger sized ball probe 432 is provided with a different angled connection to the foot piece 430. And the largest sized ball probe 442 is provided with a smaller angled connection to the foot piece 440. FIG. 4 provides an example of the various ball probe devices 400 that may allow a surgeon to evaluate the opening to the intervertebral foramina space of a patient. The different angles enable the surgeon to manipulate the ball probe device 400 into the proper area of the patient, and the different size of ball probes 412, 422, 432, 442 provide the measurement of the access area to the intervertebral foramina. The surgeon may start with the largest ball probe 442, and if that is unable to access the intervertebral foramina, then he or she will move to the next smaller ball probe 432. Once the surgeon finds the proper ball probed 412, 422, 432, 442, he or she can better understand the obstruction of access to the intervertebral foramina. Due to the importance of the spine, the spinal column, the intervertebral foramina, and the exiting nerve roots, the ball probe 412, 422, 432, 442 is designed as a perfect sphere to avoid causing any damage to any dural elements or exiting nerve roots in their corresponding intervertebral foramina.

Figure 5:
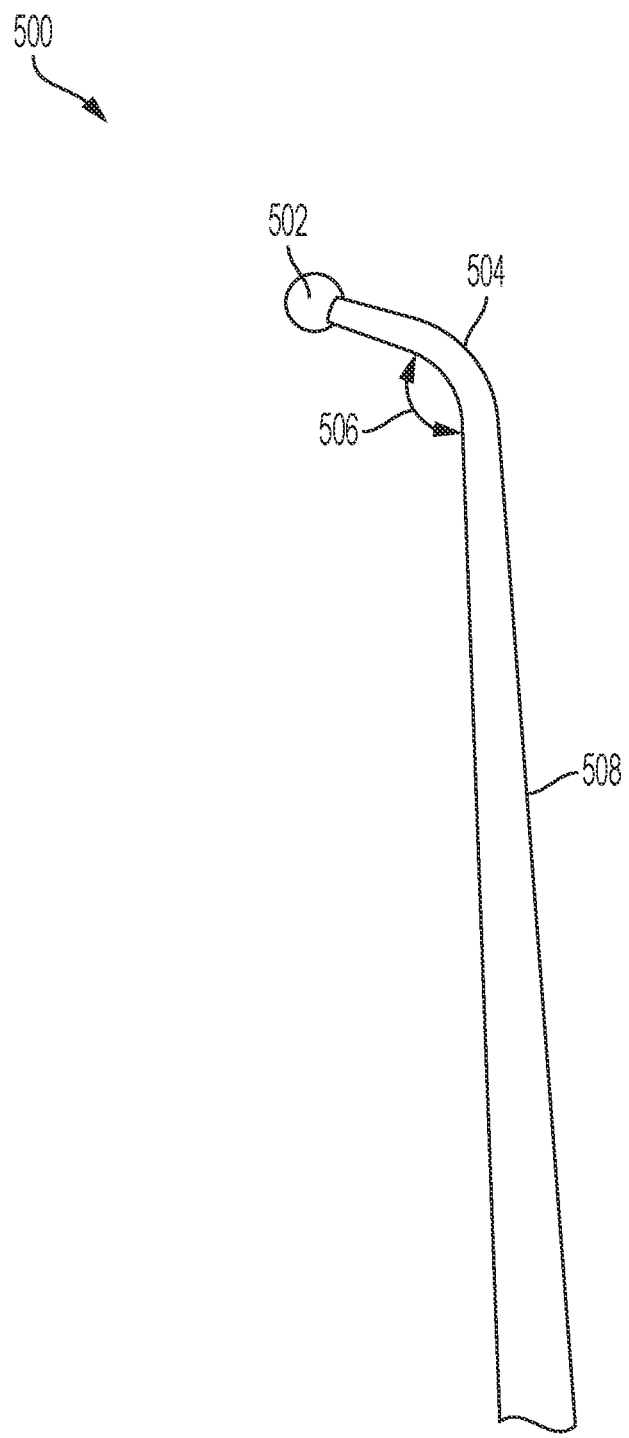
FIG. 5 shows a view of a ball tip portion of a ball probe device that has been used in prior methods to evaluate a space in the intervertebral foramina.

FIG. 5 shows a view of a ball tip portion 502 of a ball probe device 500 that has been used in prior methods to evaluate a space in the intervertebral foramina. A foot piece 504 connects a shaft 508 to the ball tip portion 502 of the ball probe device 500. The foot piece 504 portion is connected to the shaft 508 through an angle 506 for providing the surgeon with better access to the intervertebral foramina. While the ball probe devices 400, 500 are proper for evaluating an access to the intervertebral foramina, they fail to assist with removing any tissue, bone, or other materials that may be restricting access. The prior devices mentioned above in the Background of the Invention have then been used to remove any tissue, bone, or other materials that may be restricting access to the intervertebral foramina. Then the ball probe devices 400, 500 could be used later in the procedure to evaluate progress.

Due to the drawbacks of the prior devices, the present invention offers a better solution for removing tissue, bone, or other material from the intervertebral foramina. This may be accomplished through an open and minimally invasive foraminotomy, which is primarily done in the lumbar spine, but may also be done in the thoracic or cervical spine. The present invention may also be used for open and minimally invasive facet osteotomies (facetectomy) to assist with spondylolishtesis.

Figure 6:
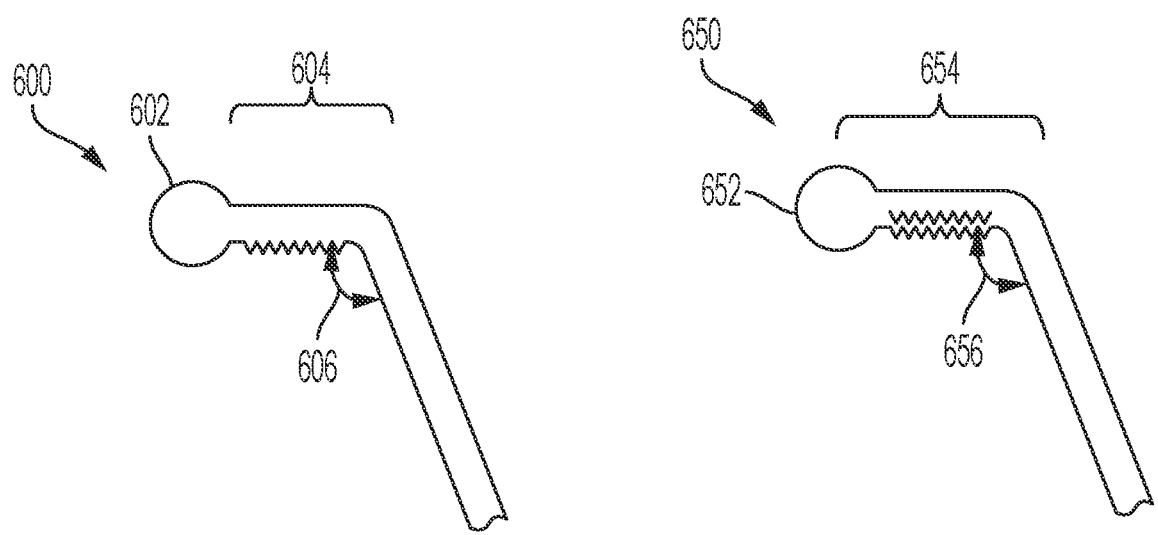
FIG. 6 shows a view of a foot piece portion and a ball tip portion of the ball probe ultrasonic bone removal device according to certain embodiments of the claimed invention.

FIG. 6 shows a view of a foot piece portion 604, 654 and a ball tip portion 602, 652 of the ball probe ultrasonic bone removal device 600, 650 according to certain embodiments of the claimed invention. Ultrasonic a removal devices have been used in the past by surgeons to remove bone, cartilage, or tissue in other procedures. Further description of the ultrasonic bone removal ature of the claimed invention will be described in detail below. This ball probe ultrasonic bor e removal device 600, 650 is designed to provide the evaluation features of the ball tip portion 602, 652 and the bone and tissue removal features of the foot piece portion 604, 654. Serrations or coarse surfaces on the foot piece 604, 654 in conjunction with ultrasonic movement enable the ball probe ultrasonic bone removal device 600, 650 to remove bone and tissue. As shown in FIG. 6, the serrations or coarse surfaces are located on the inside angle 606, 656 of the device 600. As discussed above, this angle 606, 656 and the size of the ball tip portion 602, 652 may vary between devices or attachments to devices. The amount of coverage for the serrations or coarse surfaces may also vary between devices or attachments to devices. Foot piece portion 654 shows further coverage of serrations around the circumference of the foot piece than foot piece portion 604. The ball tip portion 602, 652 is designed as a perfect sphere to avoid causing any damage to the surrounding nerves in the intervertebral foramina.

Figure 7:
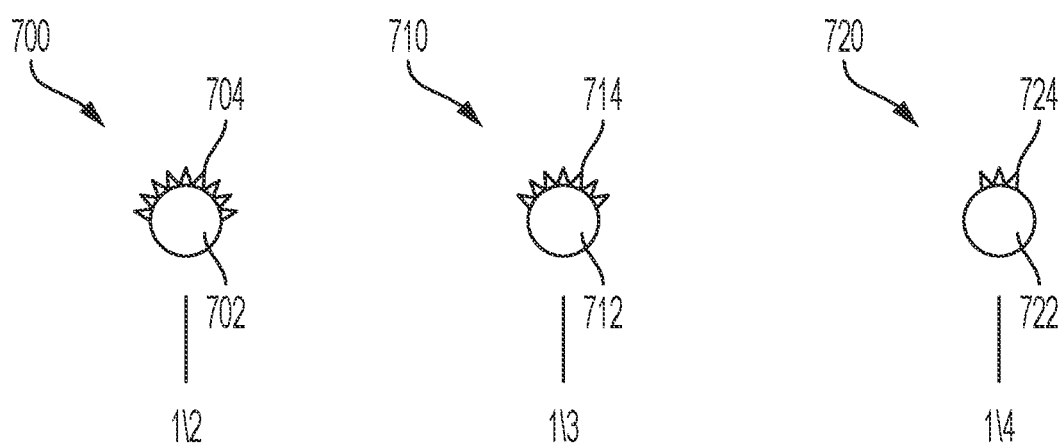
FIG. 7 shows numerous cross-section views of a foot piece portion of the ball probe ultrasonic bone removal device according to certain embodiments of the claimed invention.

FIG. 7 shows numerous cross-section views of a foot piece portion 700, 710, 720 of the ball probe ultrasonic bone removal device 600 according to certain embodiments of the claimed invention. These cross-section views further illustrate the coverage for the serrations or coarse surfaces (with protrusions) in the foot piece portion. For example, foot piece cross-section 702 shows serrati coverage 704 of about one-half (50%) of the circumference of the foot piece. Foot piece cross-section 712 shows serration coverage 714 of about one-third (33%) of the circumference of the foot piece, and foot piece section 722 shows serration coverage 724 of about one-fourth (25%) of the circumference of the foot piece. Depending on the procedure, the surgeon may want to a version of the ball probe ultrasonic bone removal device 600 that removes more or less bone and tissue. In some embodiments, the foot piece cross-section 702 may remove more bone and tissue at a faster pace than the foot piece cross-section 722. The sides without the serrations or coarse surfaces should be smooth in most embodiments of the present invention.

Figure 8:
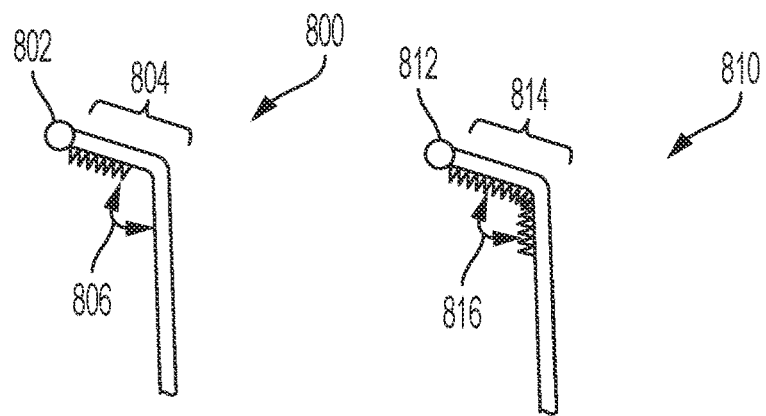
FIG. 8 shows numerous views of a foot piece portion and ball tip portion of the ball probe ultrasonic bone removal device according to certain embodiments of the claimed invention.
Figure 8:
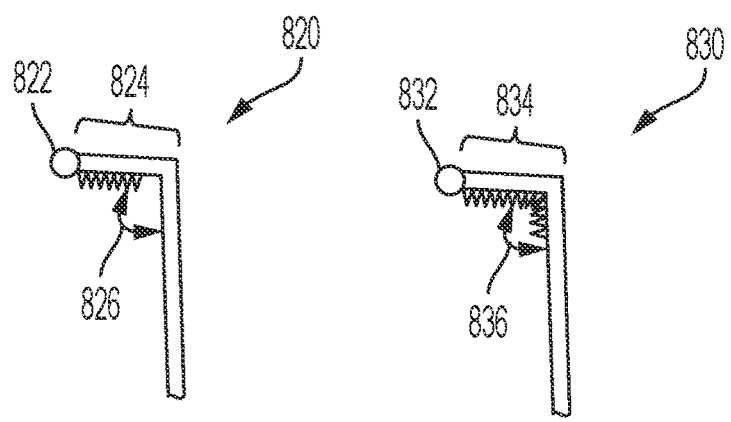
Figure 8:
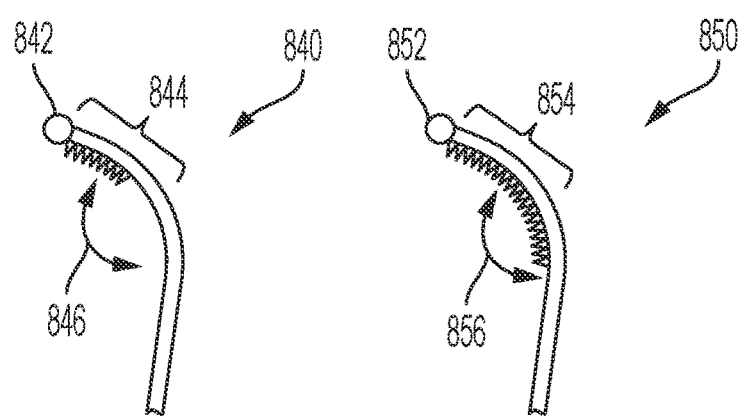

FIG. 8 shows numerous views of a foot piece portion 804, 814, 824, 834, 844, 854 and ball tip portion 802, 812, 822, 832, 842, 852 of the ball probe ultrasonic bone removal device 800, 810, 820, 830, 840, 850 according to certain embodiments of the claimed invention. In addition to the coverage of serration or coarse surfaces around the circumference of the foot piece portion, the length and location of the coverage of serration or coarse surfaces on the foot piece may be different. Ball probe ultrasonic removal device 800 shows an angle 806 that is larger than 90 degrees, and a serration pattern that is only on the upper portion of the foot piece 804 that is closest to the ball tip portion 802. Ball probe ultrasonic removal device 810 shows an angle 816 that is a larger than 90 degrees, and a serration pattern that is on the upper portion of the foot piece 814 and a lower portion of a shaft. Thus, the portion of the angle 816 that leads to the ball tip portion 812 and the portion of the angle 816 that leads to the handle (not shown) are covered in serrations. The serrations or coarse surface may also be described as surfaces with protrusions such as teeth, edges, spikes, blades, etc.

Ball probe ultrasonic removal device 820 shows an angle 826 that is close to 90 degrees, and a serration pattern that is only on the upper portion of the foot piece 824 that is closest to the ball tip portion 822. Ball probe ultrasonic removal device 830 shows an angle 836 that is close to 90 degrees, and a serration pattern that is on the upper portion of the foot piece 834 and a lower portion of a shaft. Thus, the portion of the angle 836 that leads to the ball tip portion 832 and the portion of the angle 836 that leads to the handle (not shown) are covered in serrations. Ball probe ultrasonic removal device 840 shows an angle 846 that is close to 120 degrees, and a serration pattern that is only on the upper portion of the foot piece 844 that is closest to the ball tip portion 842. Ball probe ultrasonic removal device 850 shows an angle 856 that is close to 120 degrees, and a serration pattern that is on the upper portion of the foot piece 854 and a lower portion of a shaft. Thus, the portion of the angle 856 that leads to the ball tip portion 852 and the portion of the angle 856 that leads to the handle (not shown) are covered in serrations. FIG. 8 shows the various embodiments of the present inventions. Depending on the procedure, the surgeon may want to use a version of the ball probe ultrasonic bone removal device 800, 810, 820, 830, 840, 850 that removes more or less bone and tissue. In some embodiments, serrations on the upper and lower portions of the device 810, 830, 850 may remove more bone and tissue at a faster pace than serrations only on the upper portions of the device 800, 820, 840. Further, ball probe ultrasonic bone removal devices 840, 850 show more of an arc shaped angle 846, 856 than a precise angle.

In some embodiments, the angle of the foot piece may be between 90 degrees and 120 degrees, including 100 degrees and 110 degrees. In some embodiments, the amount of serration or coarse surface of the foot piece may taper along the foot piece and/or the shaft. For example, the height of the serration teeth or the coarse surface protrusions may be larger at the upper portion of the foot piece than at the lower portion. In this embodiment, the ball tip portion could provide more protection for the larger serration teeth or coarse surface protrusions at the upper portion, whereas the lower portion may be more open to the sensitive areas of the intervertebral foramina. In some embodiments, there may be a space between the ball tip portion and the serration coarse surface of the foot piece.

Figure 9:
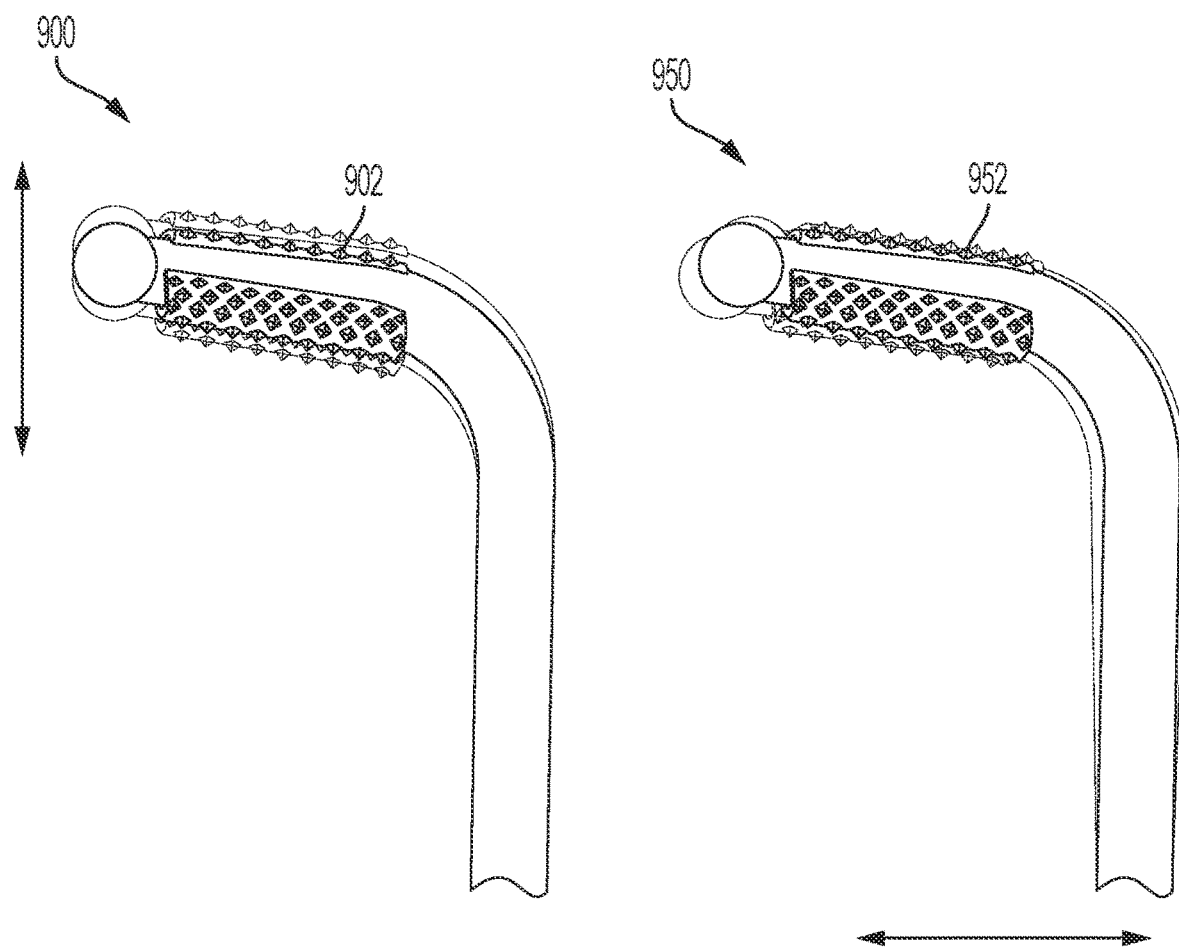
FIG. 9 shows two views of the foot piece portion of the ball probe ultrasonic bone removal device moving with longitudinal vibration and torsional oscillation according to certain embodiments of the claimed invention.

FIG. 9 shows two views of the foot piece portion 902, 952 of the ball probe ultrasonic bone removal device moving with longitudinal vibration and torsional oscillation according to certain embodiments of the claimed invention. View 900 shows the foot piece portion 902 moving with an ultrasonic movement of longitudinal vibration. With respect to the shaft and handle (not shown) of the ball probe ultrasonic bone removal device, the foot piece 902, and more particularly, the serrations or course surface of the foot piece 902 moves up and down to remove bone and tissue from the desired area. View 952 shows the foot piece portion 952 moving with an ultrasonic movement of torsional oscillation. With respect to the shaft and handle (not shown) of the ball probe ultrasonic bone removal device, the foot piece 952 rotates through an arc of movement about the center of the circle that defines a cross section of the foot piece 952. With these movements, the serrations or coarse surface on the foot piece 902, 952 remove the desired tissue and bone material. In some embodiments, the ball probe ultrasonic bone removal device may only use longitudinal vibration, only use rotational oscillation, or may use both movements. The types of movements may be controlled by the surgeon with input buttons or protrusions on the device or may be controlled through other means. For example, a computer program may be designed to control the operation of the device, including the types, speed, and orientation of ultrasonic movement.

Figure 10:
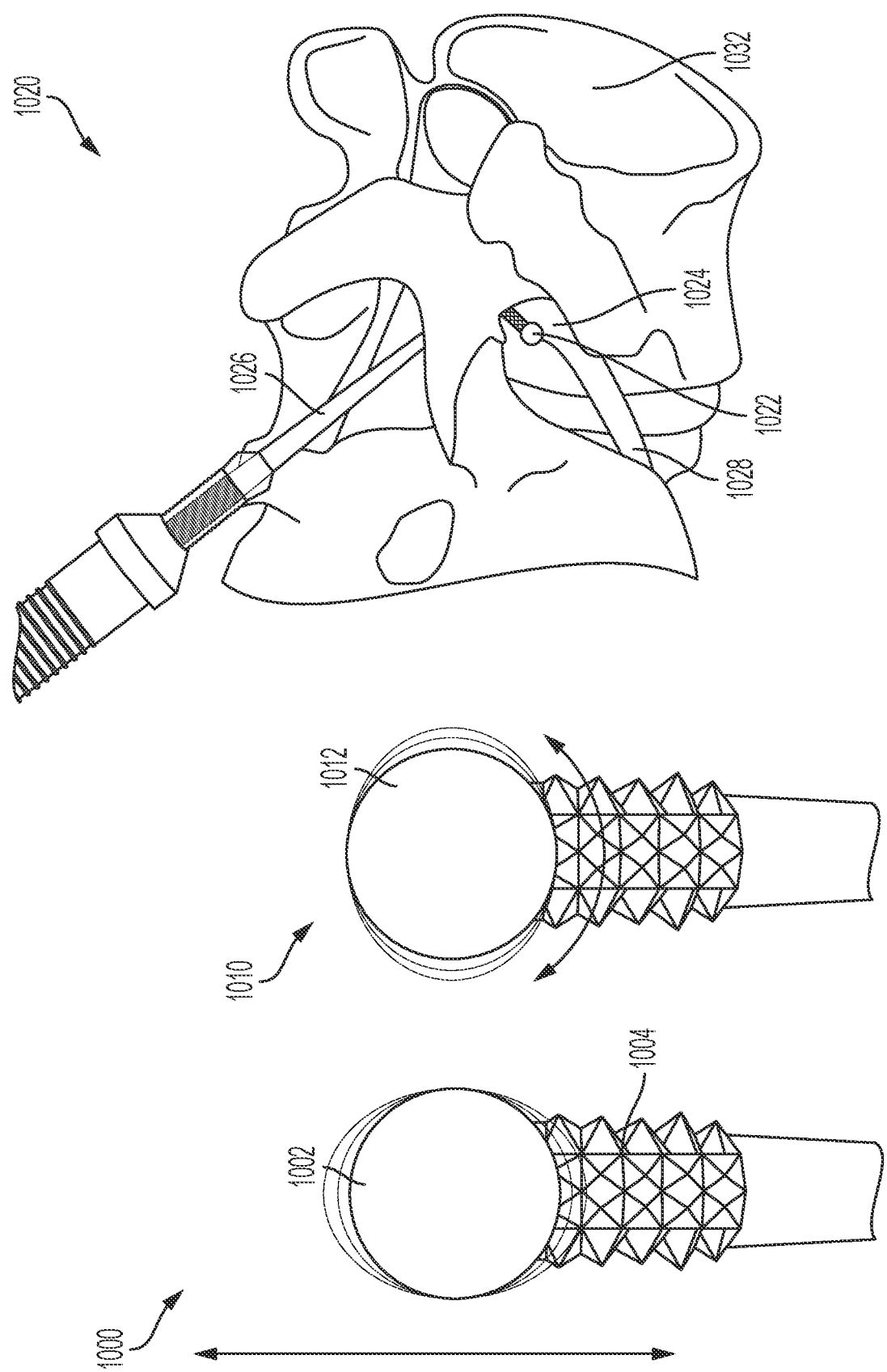
FIG. 10 shows numerous views of the ball tip portion of the ball probe ultrasonic bone removal device moving with longitudinal vibration and torsional oscillation within the intervertebral foramina according to certain embodiments of the claimed invention.

FIG. 10 shows numerous views 1000, 1010, 1020 of the ball tip portion of the ball probe ultrasonic bone removal device moving with longitudinal vibration and torsional oscillation within the intervetebral foramina according to certain embodiments of the claimed invention. View 1000 shows the foot piee portion 1002 moving with longitudinal vibration. With respect to the shaft and handle (not shown) of the ball probe ultrasonic bone removal device, the foot piece 1002, and more particularly, the serrations or coarse surface of the foot piece 1004 moves up and down to remove bone and tissue from the desired area. View 1010 shows the foot piece portion 1012 moving with torsional oscillation. The application of ultrasonic movement to the ball probe ultrasonic bone removal device may be similar to commercial devices such as the Misonix® ultrasonic bone removal devices. Drive units or motors containing an ultrasonic transducer may be used to focus the ultrasonic movement on the desired component at a desired speed or rpms. A microcontroller may be used to control the ultrasonic transducer, wherein the surgeon can control the inputs to the drive unit or motor.

View 1020 shows the ball probe ultrasonic bone removal device 1026 operating within the intervertebral foramina 1024. A vertebral body or vertebrae 1032 is also shown along with a nerve root 1028 exiting the intervertebral foramina 1024. After evaluation of the space within the intervertebral foramina 1024 with a ball tip portion 1022 of the device, the ball tip portion 1022 enables the surgeon to access the intervertebral foramina 1024 to remove bone and tissue. Once the device 1026 reaches proper location, the surgeon may turn on the device 1026 so that the serrations or coarse surface of the foot piece 1034 may ultrasonically move with longitudinal vibration and torsional oscillation to remove the desired bone and tissue from the intervertebral foramina 1024. The ball tip portion 1022 and also the smooth portions of the foot piece and shaft assist in protecting the areas of the intervertebral foramina 1024 from the serrations of the foot piece 1034.

Figure 11:
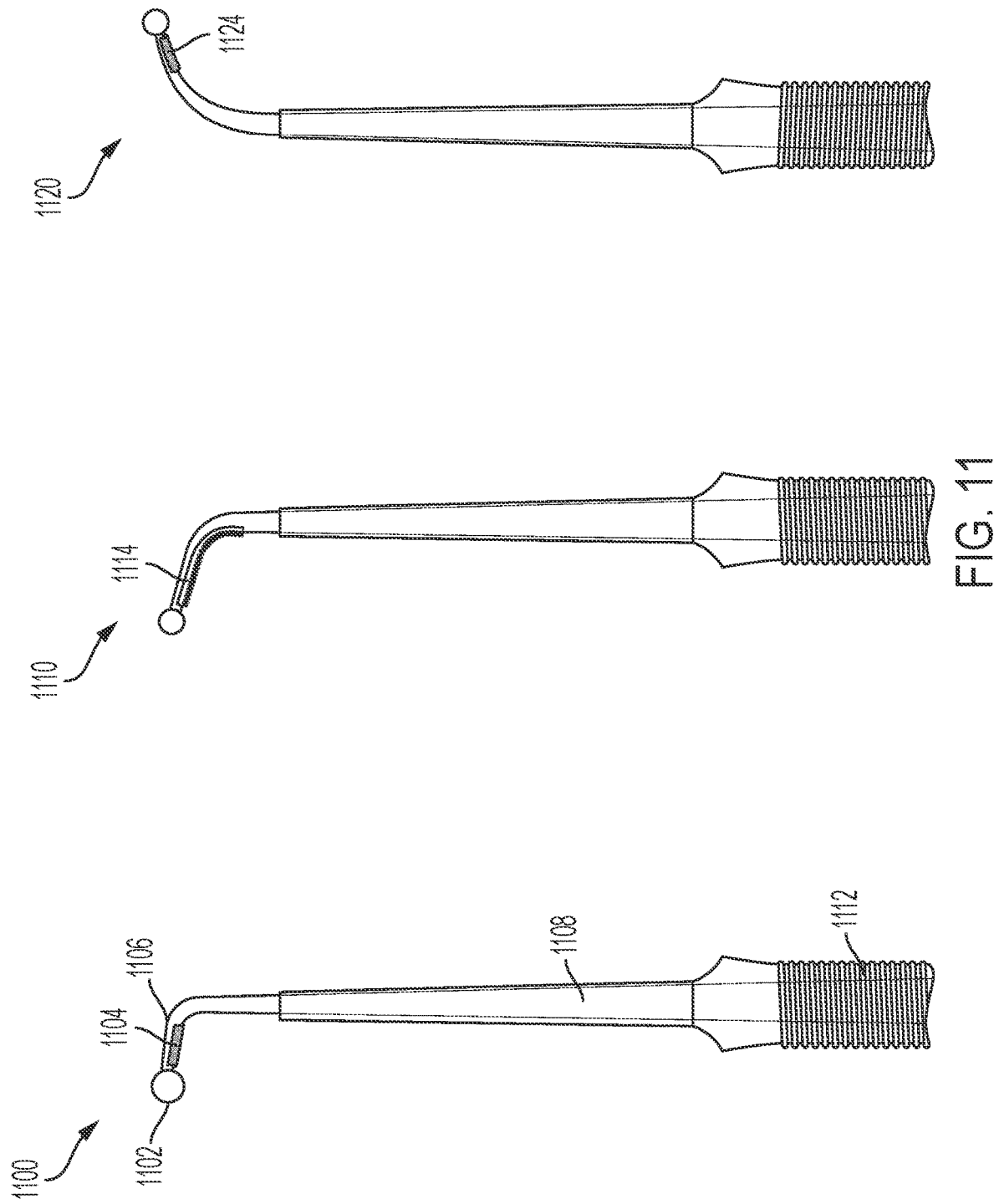
FIG. 11 shows numerous views of a ball tip portion, foot piece portion, and main shaft portion of the ball probe ultrasonic bone removal device according to certain embodiments of the claimed invention.

FIG. 11 shows n vie vs of a ball tip portion, foot piece portion, and main shaft portion of the ball probe ultrasonic bone removal device 1100, 1110, 1120 according to certain embodiments of the claimed invention. The device 1100 includes a ball tip portion 1102, foot piece portion 1106 with a serration or course surface section 1104, a shaft 1108, and a grip 1112. The grip 1112 is designed to be easily held and manipulated by a surgeon and may be made out of a flexible material li e rubber, silicone, or plastic. These materials may protect the surgeon from vibration oscillation of the device 1100. The grip 1112 may also include ribs or protrusion to assist the surgeon with holding and manipulating the device 1100. The grip 1112 may also be straight or curved and adapted to properly fit a right or left-handed surgeon. The device 1110 may be similar to device 1100 but have a different serration or coarse surface portion 1114. The device 1120 and foot piece 1124 may be similar to device 1100 but the grip or handle may be adapted to a left-handed surgeon instead of a right-handed surgeon. As will be discussed with reference to FIG. 13, the foot piece portion 1106 or the shaft 1108 may be detachable from the grip 1112 to enable numerous attachments for the same grip 1112. This way the surgeon may be able to use a single grip or handle 1112 with multiple different attachments.

Figure 12:
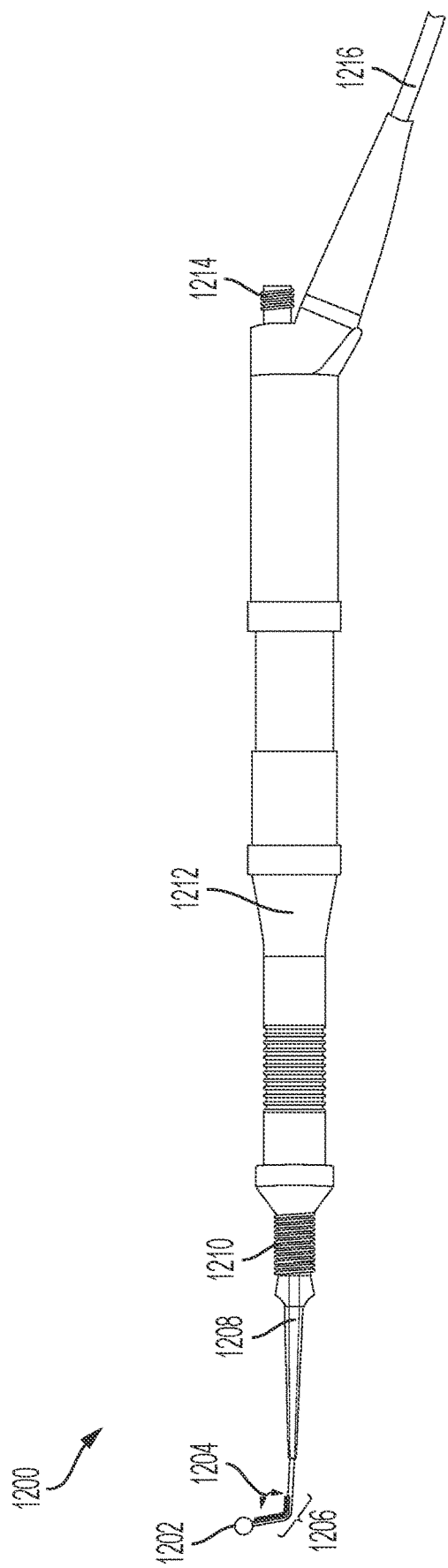
FIG. 12 shows a view of the ball probe ultrasonic bone removal device according to certain embodiments of the claimed invention.

FIG. 12 shows a view of the ball probe ultrasonic bone removal device 1200 according to certain embodiments of the claimed invention. A ball tip portion 1202 and a foot piece portion 1206 with a corresponding angle 1204 are shown. As discussed above, numerous variations of serrations or a coarse surface may exist on the foot piece portion 1206 of the device 1200. A shaft 1208 then may connect to an attachment interface 1210 on the device 1200. This attachment interface 1210 may allow numerous different ball probe attachments to be used with the device 1200. A connector 1212 may provide a connection to a power supply (not shown) through electric cord 1216. The connector 1212 may also provide a connection to a suction and/or water interface 1214. The surgeon may desire a suction feature on the device 1200 to remove the bone and tissue displaced by the ultrasonic bone removal feature of the device 1200. The surgeon may also desire a water feature to irrigate the area and improve the suction feature of the device 1200. The suction and/or water features may be controlled by the surgeon with input buttons or protrusions on the device 1200 or may be controlled through other means. For example, a computer program may be designed to control the operation of the device 1200, including the suction and/or water interface of the device 1200.

Figure 13:
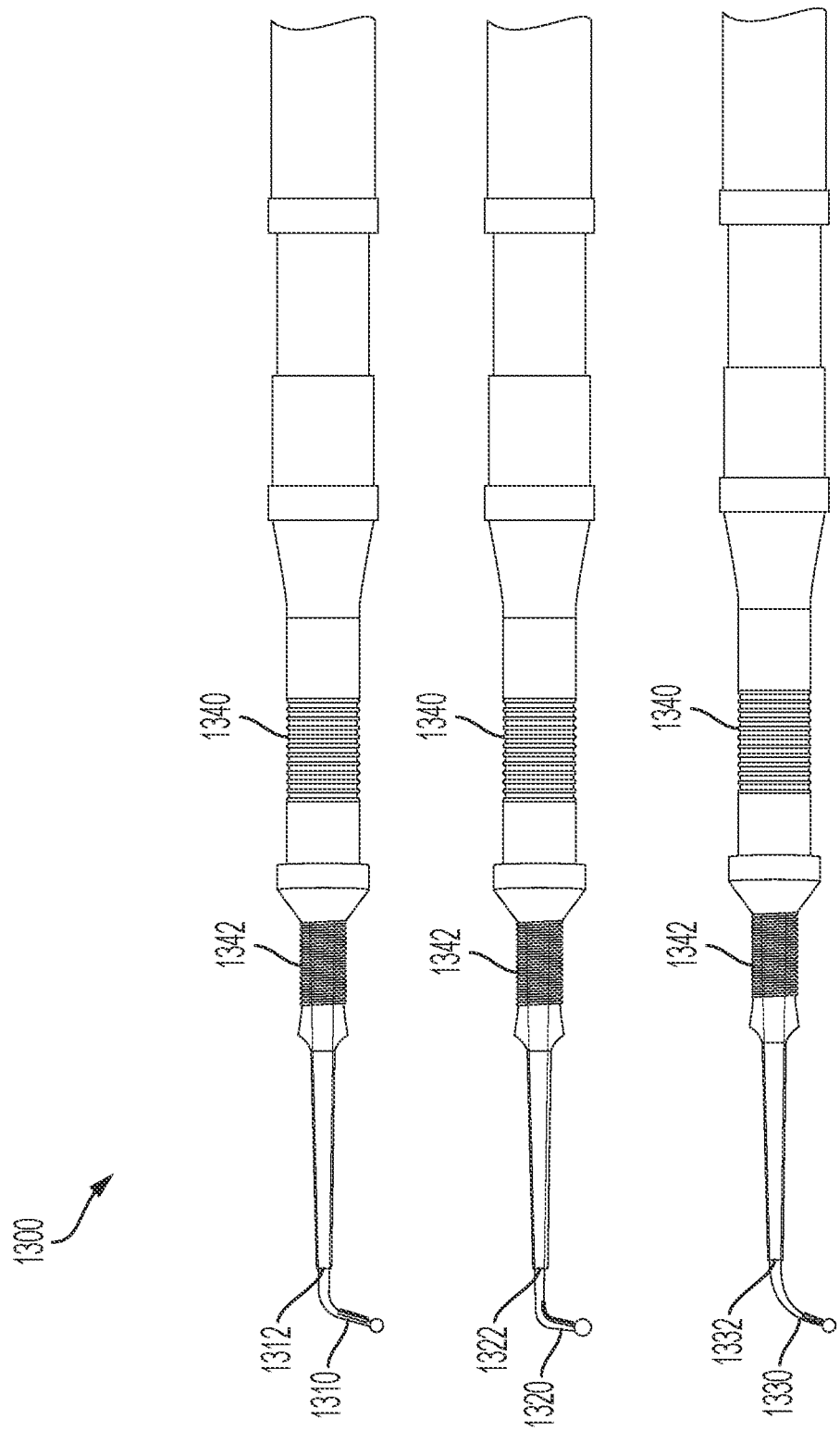
FIG. 13 shows a view of the ball probe ultrasonic bone removal device with multiple attachments according to certain embodiments of the claimed invention.

FIG. 13 shows a view of the ball probe ultrasonic bone removal device 1300 with multiple attachments according to certain embodiments of the claimed invention. An attachment interface 1342 may enable a surgeon to connect a ball probe ultrasonic bone removal attachment 1310, 1320, 1330 to the grip or handle 1340. Attachments portions 1312, 1322, 1332 may be connected to the attachment interface 1342 through various mechanisms. Attachment portions 1312, 1322, and 1332 are similar to drill bits in that they can be quickly attached and removed from attachment interface 1342. In some embodiments, the attachment portions 1312, 1322, 1332 may screw on to the attachment interface 1342. In other embodiments, the attachment portions 1312, 1322, 1332 may slide on or into the attachment interface 1342 and lock into place. A protrusion (not shown) may be used to confirm that the attachment portion 1312, 1322, 1332 is fully locked into place. The attachment interface 1342 and the corresponding attachment portions 1312, 1322, 1332 may take many different forms. Also, as shown in FIG. 13, the serration portions and the corresponding angles of the foot pieces may vary to provide the surgeon with flexibility for the procedure. The attachments 1310, 1320, 1330 may be disposable, while the grip or connector 1340 may be reusable.

Figure 14:
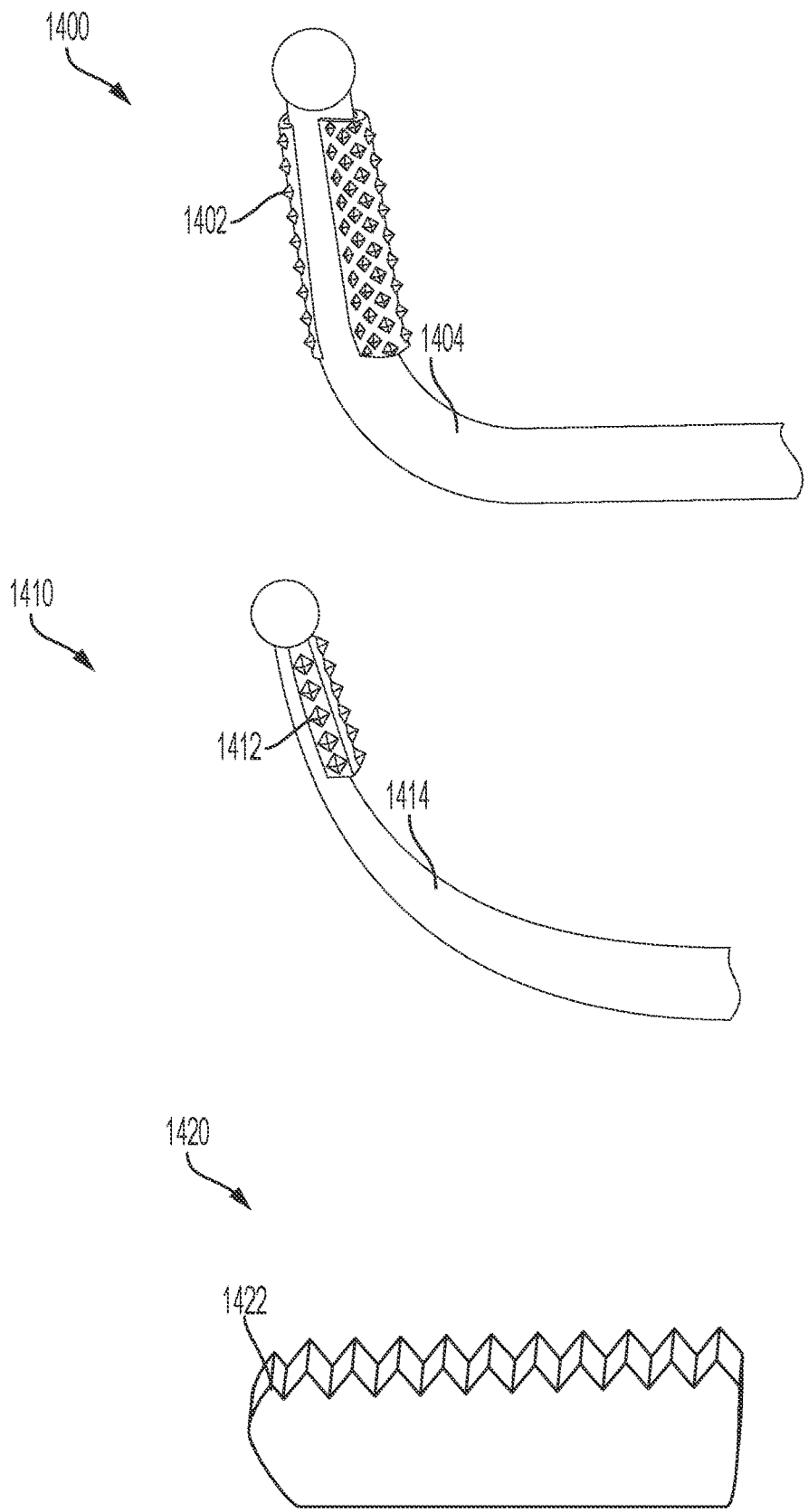
FIG. 14 shows numerous serration or coarse surface patterns for the ball probe ultrasonic bone removal device according to certain embodiments of the claimed invention.

FIG. 14 shows numerous serrations or coarse surface patterns 1400, 1410, 1420 for the ball probe ultrasonic bone removal device according to certain embodiments of the claimed invention. Coarse patterns 1402 and 1412 show patterns that could be applied to the corresponding foot pieces 1404 and 1414 of the ball probe ultrasonic bone removal devices. The corresponding protrusions may be smaller or larger and may be closer or further away from each other. Serration pattern or knife edge 1422 shows a pattern that could be applied to the corresponding foot piece of the ball probe ultrasonic bone removal device. Depending upon the type of procedure and the area of bone and tissue to be removed, different serrations or coarse surface patterns (with corresponding protrusions) 1400, 1410, 1420 may be desired. Further, the device may be adjusted to apply longitudinal vibration for some patterns, rotational oscillation for some patterns, or both with some patterns. For example, depending upon the orientation of the serration pattern or knife edge 1422, only one type of movement may be desired.

As mentioned above, the features of the ball probe ultrasonic bone removal device may be controlled by input buttons, protrusions, or a screen on the device. These inputs could include type of ultrasonic movement (longitudinal vibration or rotational oscillation), speed of ultrasonic movement (4,000 to 10,000 rpms), depth of ball probe, suction, irrigation, and other methods of operation. These inputs may also be controlled through a computer program that interfaces with the ball probe ultrasonic bone removal device and allows the surgeon to apply the proper inputs to the device for the corresponding procedure. The surgeon may apply these inputs to the device through a screen or interface that is in wired or wireless connection with the device.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A ball probe device for use with a patient comprising:
   a shaft that is connected to a handle;
   a foot piece that is configured to be connected to said shaft, wherein said connection is an angular connection with an inner portion that is approximately half of a circumference of a cross-section of the angular connection located on the inside of the angular connection and an outer portion that is a supplementary portion of the circumference of said cross-section of said angular connection;

a ball tip that is configured to be spherical with a surface without protrusions and connected to said foot piece, wherein said ball tip has a larger diameter than a cross-section of an adjacent portion of said foot piece;

wherein at least a first portion of a surface of said foot piece is at least partially covered in a first set of protrusions, wherein said at least a portion of said surface is less than an entire circumference of said foot piece, and wherein at least a second portion of a surface of said shaft is at least partially covered in a second set of protrusions, wherein said at least one second portion of said surface is less than an entire circumference of said shaft;

wherein a third set of protrusions covers a majority of said inner portion of said angular connection, and wherein said outer portion of said angular connection comprises a surface without protrusions; and wherein an ultrasonic movement is configured to be applied to said first set of protrusions, said second set of protrusions, and said third set of protrusions.

2. The ball probe device of claim 1 wherein said first set of protrusions comprise serrations.

3. The ball probe device of claim 1 wherein said portion of said surface of said foot piece covered in said first set of protrusions is configured to be about 50% of said circumference of said surface of said foot piece or less.

4. The ball probe device of claim 1 wherein said portion of said surface of said foot piece covered in said first set of protrusions is configured to be about 33% of said circumference of said surface of said foot piece or less.

5. The ball probe device of claim 1 wherein said portion of said surface of said shaft covered in said second set of protrusions is configured to be about 50% of said circumference of said surface of said shaft or less.

6. The ball probe device of claim 1 wherein at least a portion of a surface of said shaft is at least partially covered in said second set of protrusions and said second set of protrusions comprise serrations.

7. The ball probe device of claim 1 wherein said ultrasonic movement comprises longitudinal vibration or rotational oscillation.

8. The ball probe device of claim 1 wherein said handle is further configured to provide suction to a vertebral foramina of said patient.

9. The ball probe ultrasonic device of claim 1 wherein said handle is further configured to provide irrigation to a vertebral foramina of a patient.

10. An ultrasonic bone removal device for use with a patient comprising:
a shaft that is configured to be manipulated by a user;
a foot piece that is configured to be connected to said shaft, wherein there is an angular connection between said shaft and said foot piece, with an inner surface that is approximately half of the circumference of said angular connection located on the inside of the angular connection and an outer surface that is a supplementary portion of the circumference of said angular connection; and
a ball probe that is configured to be connected to said foot piece, wherein said ball probe is spherical with a smooth surface, wherein said ball probe has a larger diameter than a cross-section of an adjacent portion of said foot piece;

wherein a first portion of a circumference of said foot piece comprises a first coarse surface that is less than a said circumference of said foot piece, and wherein a second portion of a circumference of said shaft comprises a second coarse surface that is less than a circumference of said shaft;

wherein a third coarse surface covers a majority of said inner surface of said angular connection, and wherein said outer surface of said angular connection comprises a surface without protrusions; and and wherein an ultrasonic movement is configured to be applied to said first coarse surface, said second coarse surface, and said third coarse surface.

11. The ultrasonic bone removal device of claim 10 wherein said third coarse surface includes one or more protrusions.

12. The ultrasonic bone removal device of claim 10 wherein said first coarse surface includes one or more protrusions.

13. The ultrasonic bone removal device of claim 10 wherein said ultrasonic movement comprises longitudinal vibration or rotational oscillation.

14. An ultrasonic bone removal attachment for use with a patient comprising:
a shaft that is configured to be removably connected to a handle by a user;
a foot piece that connected to said shaft, wherein said connection is an angular connection with an inner surface that is approximately half of the circumference of said angular connection located on the inside of the angular connection and an outer surface that is a supplementary portion of the circumference of said angular connection;
a spherical tip with a smooth surface that is connected to said foot piece; and
wherein at least a portion of a surface of said foot piece is a first coarse surface that is configured to displace material of said patient when an ultrasonic movement is applied to said first coarse surface;
wherein at least a portion of a surface of said shaft is a second coarse surface that is configured to displace material of said patient when said ultrasonic movement is applied to said second coarse surface; and
wherein a majority of said inner surface of said angular connection comprises a third coarse surface that is configured to displace material of said patient when an ultrasonic movement is applied to said third coarse surface, and wherein said outer surface of said angular connection is a smooth surface.

15. The ball probe ultrasonic bone removal attachment of claim 14 wherein said first coarse surface of said foot piece is configured to be about 50% of said circumference of said surface of said foot piece or less.

16. The ball probe ultrasonic bone removal attachment of claim 14 wherein said second course surface of said shaft is configured to be about 50% of said circumference of said surface of said shaft or less.

17. The ball probe ultrasonic bone removal attachment of claim 14 that is further configured to mate with an attachment interface of said handle and be disconnected from said attachment interface.

18. The ball probe ultrasonic bone removal attachment of claim 14 wherein said first coarse surface includes one or more protrusions.

* * * * *